United States Patent
Fortin et al.

(10) Patent No.: US 12,032,740 B2
(45) Date of Patent: Jul. 9, 2024

(54) CLOSED-LOOP EXTENDED REALITY STIMULUS PRESENTATION AND PERCEPTION FEEDBACK USING MULTI-CHANNEL PHYSIOLOGICAL SIGNALS

(71) Applicant: InterDigital VC Holdings, Inc., Wilmington, DE (US)

(72) Inventors: Pascal Fortin, Montreal (CA); Jeremy Cooperstock, Westmount (CA); Sanghoon Kim, Chadds Ford, PA (US)

(73) Assignee: InterDigital VC Holdings, Inc., Wilmington, DE (US)

( * ) Notice: Subject to any disclaimer, the term of this patent is extended or adjusted under 35 U.S.C. 154(b) by 0 days.

(21) Appl. No.: 18/016,179

(22) PCT Filed: Jul. 12, 2021

(86) PCT No.: PCT/US2021/041316
§ 371 (c)(1),
(2) Date: Jan. 13, 2023

(87) PCT Pub. No.: WO2022/015665
PCT Pub. Date: Jan. 20, 2022

(65) Prior Publication Data
US 2023/0251712 A1    Aug. 10, 2023

(51) Int. Cl.
*G06F 3/01* (2006.01)
*G06Q 30/0251* (2023.01)
(52) U.S. Cl.
CPC .............. *G06F 3/015* (2013.01); *G06F 3/013* (2013.01); *G06Q 30/0255* (2013.01)
(58) Field of Classification Search
CPC ..... G06F 3/015; G06F 3/013; G06Q 30/0255; G06Q 30/0242
See application file for complete search history.

(56) References Cited

U.S. PATENT DOCUMENTS

2007/0236488 A1* 10/2007 Mathan ................. G16H 50/20
                                                          345/418
2010/0250554 A1   9/2010 Shu
(Continued)

FOREIGN PATENT DOCUMENTS

CN        108304074 A     7/2018

OTHER PUBLICATIONS

International Preliminary Report on Patentability for PCT/US2021/41316 dated Jan. 17, 2023 (8pages).
(Continued)

*Primary Examiner* — Rodney Amadiz
(74) *Attorney, Agent, or Firm* — Klintworth & Rozenblat IP LLP

(57) ABSTRACT

In example embodiments, a method includes obtaining a first measurement of at least a first physiological parameter of a user from a time before presentation of an information item to the user. The information item may be, for example, a notification, an advertisement, or an emergency alert, among other possibilities. A second measurement of the first physiological parameter is obtained from a time after a beginning of the presentation of the information item to the user (e.g. during the presentation). Based at least on a comparison between the first and second measurements, a determination is made of whether the user has perceived the information item. The determination may also be based on a corruption coefficient indicating an amount by which an activity of the user is likely to interfere with the first physiological parameter.

20 Claims, 8 Drawing Sheets

(56) References Cited

U.S. PATENT DOCUMENTS

| | | | |
|---|---|---|---|
| 2011/0295142 A1 | 12/2011 | Chakravarthy | |
| 2015/0269009 A1* | 9/2015 | Faaborg | A61B 5/024 719/315 |
| 2018/0164588 A1* | 6/2018 | Leppanen | G06F 3/016 |
| 2019/0354879 A1 | 11/2019 | Van Rensburg | |

OTHER PUBLICATIONS

Pielot, M. et al., "Didn't you see my message? Predicting Attentiveness to Mobile Instant Messages." In Proceedings of the SIGCHI conference on human factors in computing systems, pp. 3319-3328. 2014 (11 pages).

Chang, Y.-J. et al., "Investigating mobile users' ringer mode usage and attentiveness and responsiveness to communication." In Proceedings of the 17th International Conference on Human-Computer Interaction with Mobile Devices and Services, pp. 6-15, 2015 (10 pages).

Sahami S. et al., "Large-scale assessment of mobile notifications." In Proceedings of the SIGCHI conference on Human factors in computing systems, 2014 (10 pages).

Andersen, H. et al., "Modeling vibrotactile detection by logistic regression." In Proceedings of the 7th Nordic Conference on Human-Computer Interaction: Making Sense Through Design, 2012 (5 pages).

Blum, J. et al., "Improving haptic feedback on wearable devices through accelerometer measurements." In Proceedings of the 28th Annual ACM Symposium on User Interface Software & Technology, pp. 31-36. 2015, (6 pages).

Fortin, P. et al., "Detecting perception of smartphone notifications using skin conductance responses." In Proceedings of the 2019 CHI Conference on Human Factors in Computing Systems, pp. 1-9. May 2019 (9 pages).

Jerritta, S., et al., "Physiological signals based human emotion recognition: a review." In 2011 IEEE 7th international colloquium on signal processing and its applications, pp. 410-415. IEEE, 2011 (6 pages).

International Search Report and Written Opinion for PCT/US2021/041316 dated Nov. 10, 2021 (11 pages).

* cited by examiner

CLOSED-LOOP EXTENDED REALITY STIMULUS PRESENTATION AND PERCEPTION FEEDBACK USING MULTI-CHANNEL PHYSIOLOGICAL SIGNALS

CROSS-REFERENCE TO RELATED APPLICATIONS

The present application is a national stage application under 35 U.S.C. § 371 of International Application No. PCT/US2021/041316, entitled "CLOSED-LOOP EXTENDED REALITY STIMULUS PRESENTATION AND PERCEPTION FEEDBACK USING MULTI-CHANNEL PHYSIOLOGICAL SIGNALS," filed on Jul. 12, 2021, which is a claims benefit under 35 U.S.C. § 119(e) from U.S. Provisional Patent Application Ser. No. 63/052,313, entitled "CLOSED-LOOP EXTENDED REALITY STIMULUS PRESENTATION AND PERCEPTION FEEDBACK USING MULTI-CHANNEL PHYSIOLOGICAL SIGNALS," filed Jul. 15, 2020, which are hereby incorporated by reference in their entirety.

BACKGROUND

In many cases, the delivery of notifications, messages and other stimuli in extended reality (XR) systems operates in an open-loop framework. This can lead to inefficient and potentially disruptive communications with the users of such systems.

Two examples of approaches for determining a user's perception of a stimulus are as follows. One approach, used in current consumer electronics, relies on explicit user interaction. Perception is assumed once a user manually acknowledges the item or stimulus or opens the application and/or conversation that generated the notification. For example, an email notification that appears may only be dismissed once a user takes some explicit action associated with the email application, e.g., bringing the email application to the foreground, manually opening the message, or labelling it as "read". Similarly, an incoming video call within an XR environment may continue generating a notification until the user has acknowledged it, either by answering or declining the call (or a timeout occurs and the call is automatically terminated).

Another approach attempts to predict if a signal will be perceived prior to its delivery based on user context attributes and properties of the stimulus. For example, based on a user's age and current activity, a prediction may be made of whether a vibrotactile signal with a particular vibration intensity is likely to be perceived by the user. However, such reliance on discrete activity recognition as a means of predicting perception can be impractical. A prediction of whether a vibrotactile signal will be perceived can be improved by using aggregated continuous accelerometer measurements to model the amount of interfering haptic stimuli prior to the delivery of the vibrotactile signal. Such a method allows for the adjustment of stimulus properties to increase the probability that it is perceived, but it does not confirm post-presentation whether the user did, in fact, perceive the signal, without relying on explicit user interaction.

Fortin et al., in "Detecting Perception of Smartphone Notifications using Skin Conductance Responses." Proceedings of the ACM Conference on Human Factors in Computing Systems, May 4-9, 2019, Glasgow, evaluated perception of smartphone notifications using skin conductance measurements. The reliability of such a technique, however, can be diminished by user activities that corrupt the skin conductance signal.

Current XR systems are generally incapable of accurately determining whether a notification, message or in-experience stimulus has been successfully perceived without explicit interaction from the user, e.g., a button-press acknowledgement. This can result in two problematic situations. One situation is a false positive (type I error), where the system erroneously assumes that the stimulus was perceived. In such case, users may miss some content related to the XR experience or delivered through the XR system to communicate critical information related to the physical world. For example, in most systems, vibrotactile and auditory notifications are only delivered once using a simple haptic or auditory cue. Failure to perceive these cues will necessarily delay the users response to the event, potentially resulting in missed communication opportunities. Another situation is a false negative (type II error), where the system incorrectly assumes that a notification has not been perceived. In such case, it may repeat the notification redundantly, significantly disrupting users as they are engaging with their primary activity. For example, an incoming call will keep "ringing" until the user decides either to answer or dismiss it. Similarly, a visual notification may remain on the screen for an extended period of time, despite the fact that it was perceived by the user. These stimuli place undue demands on the user's limited sensory and cognitive resources, ultimately impacting their productivity and well-being.

SUMMARY

A method according to some embodiments comprises: obtaining information indicating a current activity of a user; obtaining a first signal representing a change in a first physiological parameter of the user between a time before and a time after presentation of an information item to the user is initiated; obtaining a second signal representing a change in a second physiological parameter of the user between a time before and a time after presentation of the information item to the user is initiated; and determining, using at least the first and second signals, whether the user has perceived the information item, wherein a contribution of at least the first signal to the determination is weighted by an amount based on the current activity.

In some embodiments, obtaining the first signal comprises obtaining a first measurement of the first physiological parameter of a user from a time before presentation of the information item to the user; obtaining a second measurement of the first physiological parameter of the user from a time after the presentation of an information item to the user is initiated; and generating the first signal based on a difference between the first measurement and the second measurement.

In some embodiments, the weighting of the first signal is determined based on a corruption coefficient associated with the current activity.

In some embodiments, the corruption coefficient is based at least in part on an amount by which the current activity of the user is expected to interfere with the first physiological parameter.

In some embodiments, determining whether the user has perceived the information item comprises applying a first weight to the first signal and a second weight to the second signal, the second weight being different from the first weight.

In some embodiments, the information item is a notification.

In some embodiments, the information item is presented in an extended reality (XR) experience.

In some embodiments, the first physiological parameter is a parameter selected from the group consisting of: skin conductance, photoplethysmography (PPG), electrocardiography (ECG), electroencephalography (EEG), electromyography (EMG), electrooculography (EOG), skin temperature, heat flux, abdominal respiration, thoracic respiration, pupillometry, and gaze tracking.

In some embodiments, in response to a determination that the user has perceived the information item, dismissing the information item.

A method according to some embodiments comprises: in response to a determination to present an information item to a user, initiating a first measurement of a physiological parameter of the user for a first time period; delaying presentation of the information item to the user until after the first time period; conducting a second measurement of the physiological parameter for a second time period after initiation of the presentation of the information item to the user; and determining, based at least in part on a comparison between the first measurement and the second measurement, whether the user has perceived the information item.

Some embodiments further comprise, in response to a determination that the user has perceived the information item, dismissing the information item.

Some embodiments further comprise obtaining information indicating a current activity of a user, wherein the determination of whether the user has perceived the information item is based at least in part on the current activity of the user.

An apparatus according to some embodiments comprises a processor configured to perform at least: obtaining information indicating a current activity of a user; obtaining a first signal representing a change in a first physiological parameter of the user between a time before and a time after presentation of an information item to the user is initiated; obtaining a second signal representing a change in a second physiological parameter of the user between a time before and a time after presentation of the information item to the user is initiated; and determining, using at least the first and second signals, whether the user has perceived the information item, wherein a contribution of at least the first signal to the determination is weighted by an amount based on the current activity.

In example embodiments, a method includes obtaining a first measurement of at least a first physiological parameter of a user from a time before presentation of an information item to the user. The information item may be, for example, a notification, an advertisement, or an emergency alert, among other possibilities. The information item may be another experience-relevant event or information, such as an event occurring in a movie, a games, or the like. A second measurement of the first physiological parameter is obtained from a time after a beginning of the presentation of the information item to the user (e.g. during the presentation). Based at least on a comparison between the first and second measurements, a determination is made of whether the user has perceived the information item. The determination may also be based on a corruption coefficient indicating an amount by which an activity of the user is likely to interfere with the first physiological parameter.

In some embodiments, the corruption coefficient is based on a determined activity being performed by the user. In some embodiments, the corruption coefficient is further based on motion specific to an on-body measurement site, such as the user's arms or legs.

In some embodiments, pre- and post-presentation measurements of a plurality of physiological parameters (possibly weighted based on respective corruption coefficients) are used in determining whether the user has perceived the information item.

EXAMPLE NETWORKS FOR IMPLEMENTATION OF THE EMBODIMENTS

Figure 1A:
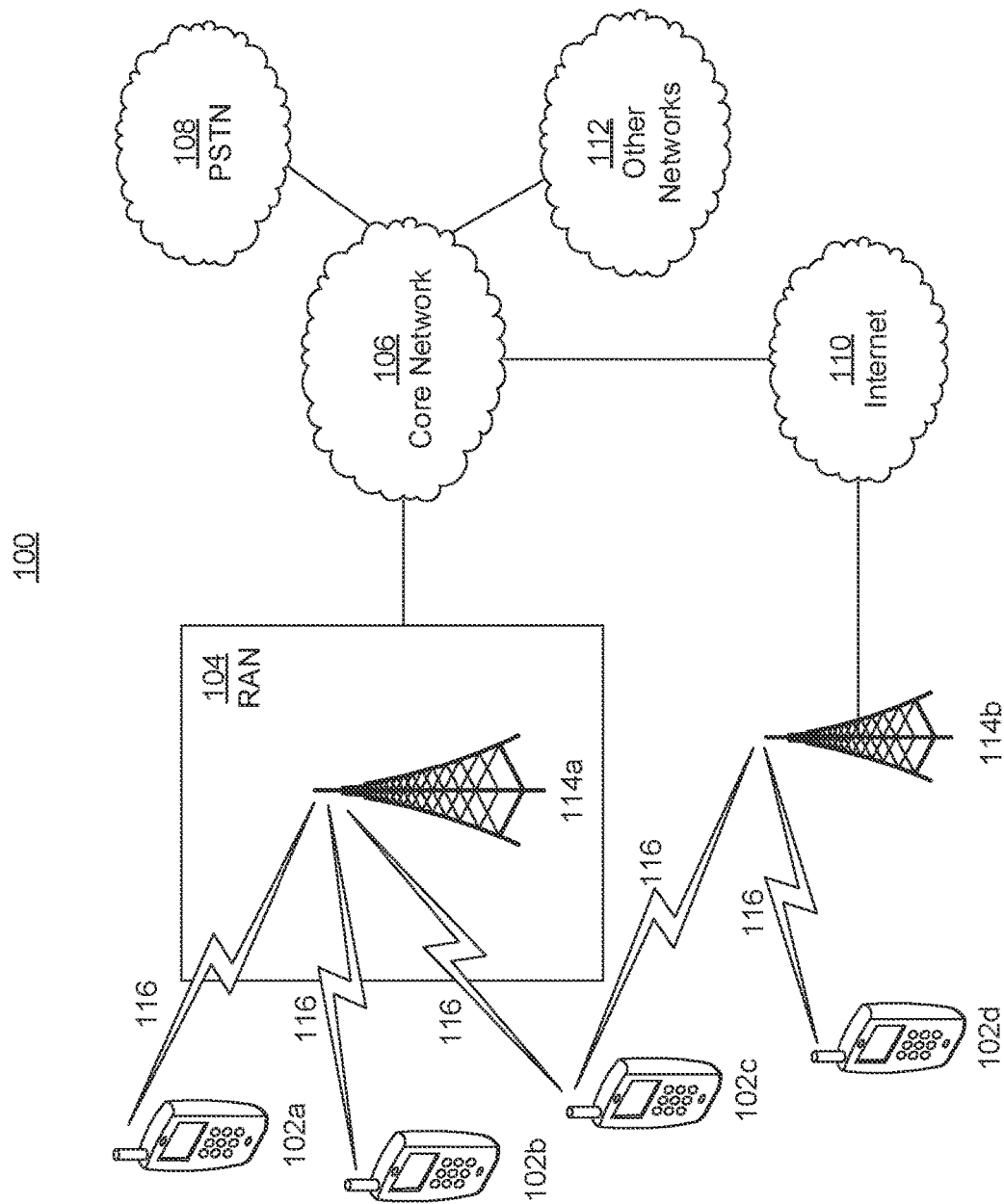
FIG. 1A is a system diagram illustrating an example communications system in which one or more disclosed embodiments may be implemented.

FIG. 1A is a diagram illustrating an example communications system 100 in which one or more disclosed embodiments may be implemented. The communications system 100 may be a multiple access system that provides content, such as voice, data, video, messaging, broadcast, etc., to multiple wireless users. The communications system 100 may enable multiple wireless users to access such content through the sharing of system resources, including wireless bandwidth. For example, the communications systems 100 may employ one or more channel access methods, such as code division multiple access (CDMA), time division multiple access (TDMA), frequency division multiple access (FDMA), orthogonal FDMA (OFDMA), single-carrier FDMA (SC-FDMA), zero-tail unique-word DFT-Spread OFDM (ZT UW DTS-s OFDM), unique word OFDM (UW-OFDM), resource block-filtered OFDM, filter bank multicarrier (FBMC), and the like.

As shown in FIG. 1A, the communications system 100 may include wireless transmit/receive units (WTRUs) 102*a*, 102*b*, 102*c*, 102*d*, a RAN 104, a CN 106, a public switched telephone network (PSTN) 108, the Internet 110, and other networks 112, though it will be appreciated that the disclosed embodiments contemplate any number of WTRUs, base stations, networks, and/or network elements. Each of the WTRUs 102*a*, 102*b*, 102*c*, 102*d* may be any type of device configured to operate and/or communicate in a wireless environment. By way of example, the WTRUs 102*a*, 102*b*, 102*c*, 102*d*, any of which may be referred to as a "station" and/or a "STA", may be configured to transmit and/or receive wireless signals and may include a user equipment (UE), a mobile station, a fixed or mobile subscriber unit, a subscription-based unit, a pager, a cellular telephone, a personal digital assistant (PDA), a smartphone, a laptop, a netbook, a personal computer, a wireless sensor, a hotspot or Mi-Fi device, an Internet of Things (IoT) device, a watch or other wearable, a head-mounted display (HMD), a vehicle, a drone, a medical device and applications (e.g., remote surgery), an industrial device and applications (e.g., a robot and/or other wireless devices operating in an industrial and/or an automated processing chain contexts), a consumer electronics device, a device operating on commercial and/or industrial wireless networks, and the like. Any of the WTRUs 102a, 102b, 102c and 102d may be interchangeably referred to as a UE.

The communications systems 100 may also include a base station 114a and/or a base station 114b. Each of the base stations 114a, 114b may be any type of device configured to wirelessly interface with at least one of the WTRUs 102a, 102b, 102c, 102d to facilitate access to one or more communication networks, such as the CN 106, the Internet 110, and/or the other networks 112. By way of example, the base stations 114a, 114b may be a base transceiver station (BTS), a Node-B, an eNode B, a Home Node B, a Home eNode B, a gNB, a NR NodeB, a site controller, an access point (AP), a wireless router, and the like. While the base stations 114a, 114b are each depicted as a single element, it will be appreciated that the base stations 114a, 114b may include any number of interconnected base stations and/or network elements.

The base station 114a may be part of the RAN 104, which may also include other base stations and/or network elements (not shown), such as a base station controller (BSC), a radio network controller (RNC), relay nodes, etc. The base station 114a and/or the base station 114b may be configured to transmit and/or receive wireless signals on one or more carrier frequencies, which may be referred to as a cell (not shown). These frequencies may be in licensed spectrum, unlicensed spectrum, or a combination of licensed and unlicensed spectrum. A cell may provide coverage for a wireless service to a specific geographical area that may be relatively fixed or that may change over time. The cell may further be divided into cell sectors. For example, the cell associated with the base station 114a may be divided into three sectors. Thus, in one embodiment, the base station 114a may include three transceivers, i.e., one for each sector of the cell. In an embodiment, the base station 114a may employ multiple-input multiple output (MIMO) technology and may utilize multiple transceivers for each sector of the cell. For example, beamforming may be used to transmit and/or receive signals in desired spatial directions.

The base stations 114a, 114b may communicate with one or more of the WTRUs 102a, 102b, 102c, 102d over an air interface 116, which may be any suitable wireless communication link (e.g., radio frequency (RF), microwave, centimeter wave, micrometer wave, infrared (IR), ultraviolet (UV), visible light, etc.). The air interface 116 may be established using any suitable radio access technology (RAT).

More specifically, as noted above, the communications system 100 may be a multiple access system and may employ one or more channel access schemes, such as CDMA, TDMA, FDMA, OFDMA, SC-FDMA, and the like. For example, the base station 114a in the RAN 104 and the WTRUs 102a, 102b, 102c may implement a radio technology such as Universal Mobile Telecommunications System (UMTS) Terrestrial Radio Access (UTRA), which may establish the air interface 116 using wideband CDMA (WCDMA). WCDMA may include communication protocols such as High-Speed Packet Access (HSPA) and/or Evolved HSPA (HSPA+). HSPA may include High-Speed Downlink (DL) Packet Access (HSDPA) and/or High-Speed UL Packet Access (HSUPA).

In an embodiment, the base station 114a and the WTRUs 102a, 102b, 102c may implement a radio technology such as Evolved UMTS Terrestrial Radio Access (E-UTRA), which may establish the air interface 116 using Long Term Evolution (LTE) and/or LTE-Advanced (LTE-A) and/or LTE-Advanced Pro (LTE-A Pro).

In an embodiment, the base station 114a and the WTRUs 102a, 102b, 102c may implement a radio technology such as NR Radio Access, which may establish the air interface 116 using New Radio (NR).

In an embodiment, the base station 114a and the WTRUs 102a, 102b, 102c may implement multiple radio access technologies. For example, the base station 114a and the WTRUs 102a, 102b, 102c may implement LTE radio access and NR radio access together, for instance using dual connectivity (DC) principles. Thus, the air interface utilized by WTRUs 102a, 102b, 102c may be characterized by multiple types of radio access technologies and/or transmissions sent to/from multiple types of base stations (e.g., a eNB and a gNB).

In other embodiments, the base station 114a and the WTRUs 102a, 102b, 102c may implement radio technologies such as IEEE 802.11 (i.e., Wireless Fidelity (WiFi), IEEE 802.16 (i.e., Worldwide Interoperability for Microwave Access (WiMAX)), CDMA2000, CDMA2000 1x, CDMA2000 EV-DO, Interim Standard 2000 (IS-2000), Interim Standard 95 (IS-95), Interim Standard 856 (IS-856), Global System for Mobile communications (GSM), Enhanced Data rates for GSM Evolution (EDGE), GSM EDGE (GERAN), and the like.

The base station 114b in FIG. 1A may be a wireless router, Home Node B, Home eNode B, or access point, for example, and may utilize any suitable RAT for facilitating wireless connectivity in a localized area, such as a place of business, a home, a vehicle, a campus, an industrial facility, an air corridor (e.g., for use by drones), a roadway, and the like. In one embodiment, the base station 114b and the WTRUs 102c, 102d may implement a radio technology such as IEEE 802.11 to establish a wireless local area network (WLAN). In an embodiment, the base station 114b and the WTRUs 102c, 102d may implement a radio technology such as IEEE 802.15 to establish a wireless personal area network (WPAN). In yet another embodiment, the base station 114b and the WTRUs 102c, 102d may utilize a cellular-based RAT (e.g., WCDMA, CDMA2000, GSM, LTE, LTE-A, LTE-A Pro, NR etc.) to establish a picocell or femtocell. As shown in FIG. 1A, the base station 114b may have a direct connection to the Internet 110. Thus, the base station 114b may not be required to access the Internet 110 via the CN 106.

The RAN 104 may be in communication with the CN 106, which may be any type of network configured to provide voice, data, applications, and/or voice over internet protocol (VoIP) services to one or more of the WTRUs 102a, 102b, 102c, 102d. The data may have varying quality of service (QoS) requirements, such as differing throughput requirements, latency requirements, error tolerance requirements, reliability requirements, data throughput requirements, mobility requirements, and the like. The CN 106 may provide call control, billing services, mobile location-based services, pre-paid calling, Internet connectivity, video distribution, etc., and/or perform high-level security functions, such as user authentication. Although not shown in FIG. 1A, it will be appreciated that the RAN 104 and/or the CN 106 may be in direct or indirect communication with other RANs that employ the same RAT as the RAN 104 or a different RAT. For example, in addition to being connected to the RAN 104, which may be utilizing a NR radio technology, the CN 106 may also be in communication with another RAN (not shown) employing a GSM, UMTS, CDMA 2000, WiMAX, E-UTRA, or WiFi radio technology.

The CN 106 may also serve as a gateway for the WTRUs 102a, 102b, 102c, 102d to access the PSTN 108, the Internet 110, and/or the other networks 112. The PSTN 108 may include circuit-switched telephone networks that provide plain old telephone service (POTS). The Internet 110 may include a global system of interconnected computer networks and devices that use common communication protocols, such as the transmission control protocol (TCP), user datagram protocol (UDP) and/or the internet protocol (IP) in the TCP/IP internet protocol suite. The networks 112 may include wired and/or wireless communications networks owned and/or operated by other service providers. For example, the networks 112 may include another CN connected to one or more RANs, which may employ the same RAT as the RAN 104 or a different RAT.

Some or all of the WTRUs 102a, 102b, 102c, 102d in the communications system 100 may include multi-mode capabilities (e.g., the WTRUs 102a, 102b, 102c, 102d may include multiple transceivers for communicating with different wireless networks over different wireless links). For example, the WTRU 102c shown in FIG. 1A may be configured to communicate with the base station 114a, which may employ a cellular-based radio technology, and with the base station 114b, which may employ an IEEE 802 radio technology.

Figure 1B:
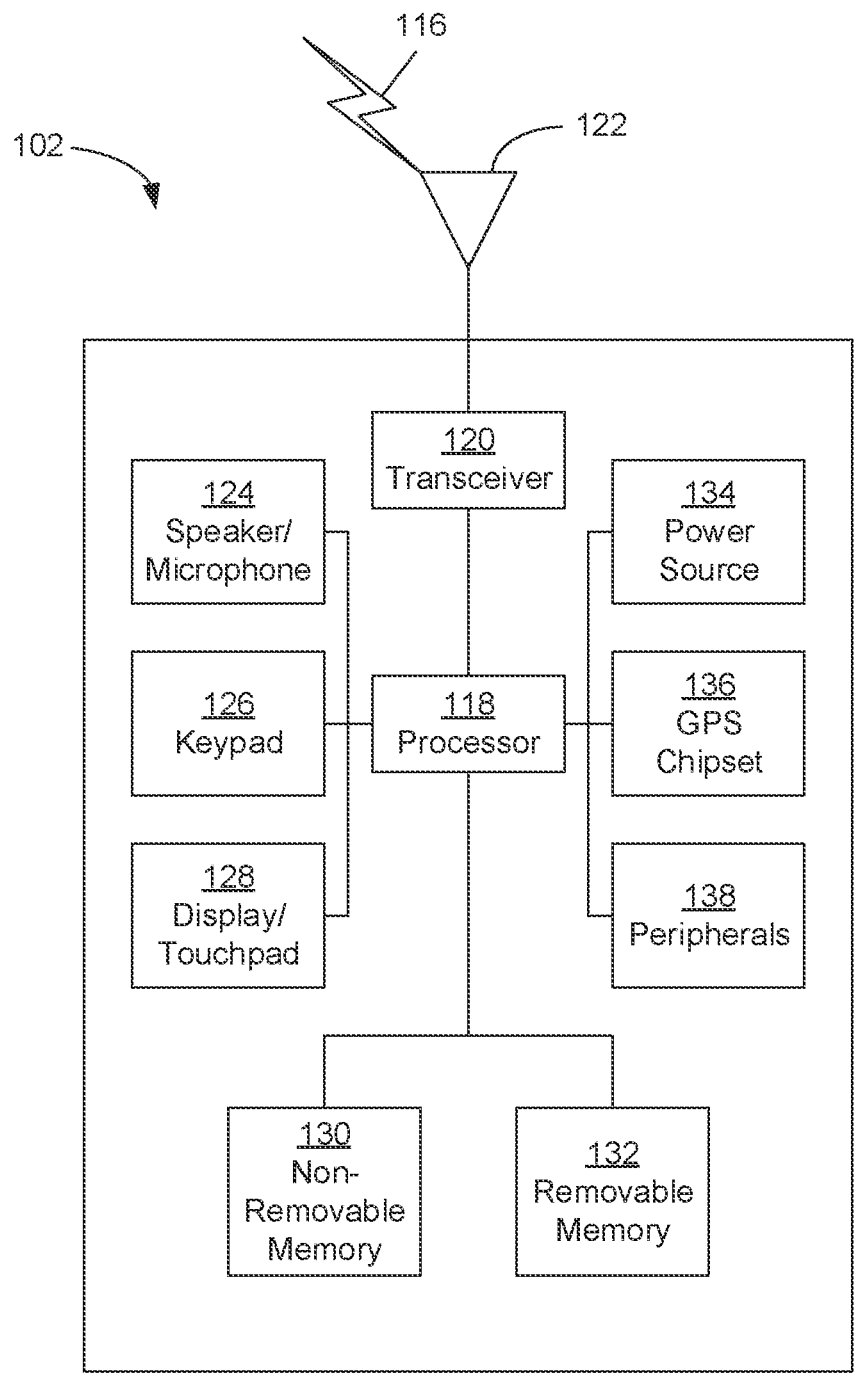
FIG. 1B is a system diagram illustrating an example wireless transmit/receive unit (WTRU) that may be used within the communications system illustrated in FIG. 1A according to an embodiment.

FIG. 1B is a system diagram illustrating an example WTRU 102. As shown in FIG. 1B, the WTRU 102 may include a processor 118, a transceiver 120, a transmit/receive element 122, a speaker/microphone 124, a keypad 126, a display/touchpad 128, non-removable memory 130, removable memory 132, a power source 134, a global positioning system (GPS) chipset 136, and/or other peripherals 138, among others. It will be appreciated that the WTRU 102 may include any sub-combination of the foregoing elements while remaining consistent with an embodiment.

The processor 118 may be a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs) circuits, any other type of integrated circuit (IC), a state machine, and the like. The processor 118 may perform signal coding, data processing, power control, input/output processing, and/or any other functionality that enables the WTRU 102 to operate in a wireless environment. The processor 118 may be coupled to the transceiver 120, which may be coupled to the transmit/receive element 122. While FIG. 1B depicts the processor 118 and the transceiver 120 as separate components, it will be appreciated that the processor 118 and the transceiver 120 may be integrated together in an electronic package or chip.

The transmit/receive element 122 may be configured to transmit signals to, or receive signals from, a base station (e.g., the base station 114a) over the air interface 116. For example, in one embodiment, the transmit/receive element 122 may be an antenna configured to transmit and/or receive RF signals. In an embodiment, the transmit/receive element 122 may be an emitter/detector configured to transmit and/or receive IR, UV, or visible light signals, for example. In yet another embodiment, the transmit/receive element 122 may be configured to transmit and/or receive both RF and light signals. It will be appreciated that the transmit/receive element 122 may be configured to transmit and/or receive any combination of wireless signals.

Although the transmit/receive element 122 is depicted in FIG. 1B as a single element, the WTRU 102 may include any number of transmit/receive elements 122. More specifically, the WTRU 102 may employ MIMO technology. Thus, in one embodiment, the WTRU 102 may include two or more transmit/receive elements 122 (e.g., multiple antennas) for transmitting and receiving wireless signals over the air interface 116.

The transceiver 120 may be configured to modulate the signals that are to be transmitted by the transmit/receive element 122 and to demodulate the signals that are received by the transmit/receive element 122. As noted above, the WTRU 102 may have multi-mode capabilities. Thus, the transceiver 120 may include multiple transceivers for enabling the WTRU 102 to communicate via multiple RATs, such as NR and IEEE 802.11, for example.

The processor 118 of the WTRU 102 may be coupled to, and may receive user input data from, the speaker/microphone 124, the keypad 126, and/or the display/touchpad 128 (e.g., a liquid crystal display (LCD) display unit or organic light-emitting diode (OLED) display unit). The processor 118 may also output user data to the speaker/microphone 124, the keypad 126, and/or the display/touchpad 128. In addition, the processor 118 may access information from, and store data in, any type of suitable memory, such as the non-removable memory 130 and/or the removable memory 132. The non-removable memory 130 may include random-access memory (RAM), read-only memory (ROM), a hard disk, or any other type of memory storage device. The removable memory 132 may include a subscriber identity module (SIM) card, a memory stick, a secure digital (SD) memory card, and the like. In other embodiments, the processor 118 may access information from, and store data in, memory that is not physically located on the WTRU 102, such as on a server or a home computer (not shown).

The processor 118 may receive power from the power source 134, and may be configured to distribute and/or control the power to the other components in the WTRU 102. The power source 134 may be any suitable device for powering the WTRU 102. For example, the power source 134 may include one or more dry cell batteries (e.g., nickel-cadmium (NiCd), nickel-zinc (NiZn), nickel metal hydride (NiMH), lithium-ion (Li-ion), etc.), solar cells, fuel cells, and the like.

The processor 118 may also be coupled to the GPS chipset 136, which may be configured to provide location information (e.g., longitude and latitude) regarding the current location of the WTRU 102. In addition to, or in lieu of, the information from the GPS chipset 136, the WTRU 102 may receive location information over the air interface 116 from a base station (e.g., base stations 114a, 114b) and/or determine its location based on the timing of the signals being received from two or more nearby base stations. It will be appreciated that the WTRU 102 may acquire location information by way of any suitable location-determination method while remaining consistent with an embodiment.

The processor 118 may further be coupled to other peripherals 138, which may include one or more software and/or hardware modules that provide additional features, functionality and/or wired or wireless connectivity. For example, the peripherals 138 may include an accelerometer, an e-compass, a satellite transceiver, a digital camera (for photographs and/or video), a universal serial bus (USB) port, a vibration device, a television transceiver, a hands free headset, a Bluetooth® module, a frequency modulated (FM) radio unit, a digital music player, a media player, a video game player module, an Internet browser, a Virtual Reality and/or Augmented Reality (VR/AR) device, an activity tracker, and the like. The peripherals 138 may include one or more sensors, the sensors may be one or more of a gyroscope, an accelerometer, a hall effect sensor, a magnetometer, an orientation sensor, a proximity sensor, a temperature sensor, a time sensor; a geolocation sensor; an altimeter, a light sensor, a touch sensor, a magnetometer, a barometer, a gesture sensor, a biometric or other physiological sensor, and/or a humidity sensor.

The WTRU 102 may include a full duplex radio for which transmission and reception of some or all of the signals (e.g., associated with particular subframes for both the UL (e.g., for transmission) and downlink (e.g., for reception) may be concurrent and/or simultaneous. The full duplex radio may include an interference management unit to reduce and or substantially eliminate self-interference via either hardware (e.g., a choke) or signal processing via a processor (e.g., a separate processor (not shown) or via processor 118). In an embodiment, the WTRU 102 may include a half-duplex radio for which transmission and reception of some or all of the signals (e.g., associated with particular subframes for either the UL (e.g., for transmission) or the downlink (e.g., for reception)).

Although the WTRU is described in FIGS. 1A-1B as a wireless terminal, it is contemplated that in certain representative embodiments that such a terminal may use (e.g., temporarily or permanently) wired communication interfaces with the communication network.

In representative embodiments, the other network 112 may be a WLAN.

A WLAN in Infrastructure Basic Service Set (BSS) mode may have an Access Point (AP) for the BSS and one or more stations (STAs) associated with the AP. The AP may have an access or an interface to a Distribution System (DS) or another type of wired/wireless network that carries traffic in to and/or out of the BSS. Traffic to STAs that originates from outside the BSS may arrive through the AP and may be delivered to the STAs. Traffic originating from STAs to destinations outside the BSS may be sent to the AP to be delivered to respective destinations. Traffic between STAs within the BSS may be sent through the AP, for example, where the source STA may send traffic to the AP and the AP may deliver the traffic to the destination STA. The traffic between STAs within a BSS may be considered and/or referred to as peer-to-peer traffic. The peer-to-peer traffic may be sent between (e.g., directly between) the source and destination STAs with a direct link setup (DLS). In certain representative embodiments, the DLS may use an 802.11e DLS or an 802.11z tunneled DLS (TDLS). A WLAN using an Independent BSS (IBSS) mode may not have an AP, and the STAs (e.g., all of the STAs) within or using the IBSS may communicate directly with each other. The IBSS mode of communication may sometimes be referred to herein as an "ad-hoc" mode of communication.

When using the 802.11ac infrastructure mode of operation or a similar mode of operations, the AP may transmit a beacon on a fixed channel, such as a primary channel. The primary channel may be a fixed width (e.g., 20 MHz wide bandwidth) or a dynamically set width via signaling. The primary channel may be the operating channel of the BSS and may be used by the STAs to establish a connection with the AP. In certain representative embodiments, Carrier Sense Multiple Access with Collision Avoidance (CSMA/CA) may be implemented, for example in in 802.11 systems. For CSMA/CA, the STAs (e.g., every STA), including the AP, may sense the primary channel. If the primary channel is sensed/detected and/or determined to be busy by a particular STA, the particular STA may back off. One STA (e.g., only one station) may transmit at any given time in a given BSS.

High Throughput (HT) STAs may use a 40 MHz wide channel for communication, for example, via a combination of the primary 20 MHz channel with an adjacent or nonadjacent 20 MHz channel to form a 40 MHz wide channel.

Very High Throughput (VHT) STAs may support 20 MHz, 40 MHz, 80 MHz, and/or 160 MHz wide channels. The 40 MHz, and/or 80 MHz, channels may be formed by combining contiguous 20 MHz channels. A 160 MHz channel may be formed by combining 8 contiguous 20 MHz channels, or by combining two non-contiguous 80 MHz channels, which may be referred to as an 80+80 configuration. For the 80+80 configuration, the data, after channel encoding, may be passed through a segment parser that may divide the data into two streams. Inverse Fast Fourier Transform (IFFT) processing, and time domain processing, may be done on each stream separately. The streams may be mapped on to the two 80 MHz channels, and the data may be transmitted by a transmitting STA. At the receiver of the receiving STA, the above described operation for the 80+80 configuration may be reversed, and the combined data may be sent to the Medium Access Control (MAC).

Sub 1 GHz modes of operation are supported by 802.11af and 802.11ah. The channel operating bandwidths, and carriers, are reduced in 802.11af and 802.11ah relative to those used in 802.11n, and 802.11ac. 802.11af supports 5 MHz, 10 MHz and 20 MHz bandwidths in the TV White Space (TVWS) spectrum, and 802.11ah supports 1 MHz, 2 MHz, 4 MHz, 8 MHz, and 16 MHz bandwidths using non-TVWS spectrum. According to a representative embodiment, 802.11ah may support Meter Type Control/Machine-Type Communications, such as MTC devices in a macro coverage area. MTC devices may have certain capabilities, for example, limited capabilities including support for (e.g., only support for) certain and/or limited bandwidths. The MTC devices may include a battery with a battery life above a threshold (e.g., to maintain a very long battery life).

WLAN systems, which may support multiple channels, and channel bandwidths, such as 802.11n, 802.11ac, 802.11af, and 802.11ah, include a channel which may be designated as the primary channel. The primary channel may have a bandwidth equal to the largest common operating bandwidth supported by all STAs in the BSS. The bandwidth of the primary channel may be set and/or limited by a STA, from among all STAs in operating in a BSS, which supports the smallest bandwidth operating mode. In the example of 802.11ah, the primary channel may be 1 MHz wide for STAs (e.g., MTC type devices) that support (e.g., only support) a 1 MHz mode, even if the AP, and other STAs in the BSS support 2 MHz, 4 MHz, 8 MHz, 16 MHz, and/or other channel bandwidth operating modes. Carrier sensing and/or Network Allocation Vector (NAV) settings may depend on the status of the primary channel. If the primary channel is busy, for example, due to a STA (which supports only a 1 MHz operating mode), transmitting to the AP, the entire available frequency bands may be considered busy even though a majority of the frequency bands remains idle and may be available.

In the United States, the available frequency bands, which may be used by 802.11ah, are from 902 MHz to 928 MHz. In Korea, the available frequency bands are from 917.5 MHz to 923.5 MHz. In Japan, the available frequency bands are from 916.5 MHz to 927.5 MHz. The total bandwidth available for 802.11ah is 6 MHz to 26 MHz depending on the country code.

In view of FIGS. 1A-1B, and the corresponding descriptions, one or more, or all, of the functions described herein may be performed by one or more emulation devices (not shown). The emulation devices may be one or more devices configured to emulate one or more, or all, of the functions described herein. For example, the emulation devices may be used to test other devices and/or to simulate network and/or WTRU functions.

The emulation devices may be designed to implement one or more tests of other devices in a lab environment and/or in an operator network environment. For example, the one or more emulation devices may perform the one or more, or all, functions while being fully or partially implemented and/or deployed as part of a wired and/or wireless communication network in order to test other devices within the communication network. The one or more emulation devices may perform the one or more, or all, functions while being temporarily implemented/deployed as part of a wired and/or wireless communication network. The emulation device may be directly coupled to another device for purposes of testing and/or may performing testing using over-the-air wireless communications.

The one or more emulation devices may perform the one or more, including all, functions while not being implemented/deployed as part of a wired and/or wireless communication network. For example, the emulation devices may be utilized in a testing scenario in a testing laboratory and/or a non-deployed (e.g., testing) wired and/or wireless communication network in order to implement testing of one or more components. The one or more emulation devices may be test equipment. Direct RF coupling and/or wireless communications via RF circuitry (e.g., which may include one or more antennas) may be used by the emulation devices to transmit and/or receive data.

DETAILED DESCRIPTION

Overview of Example Embodiments

Example embodiments use changes in physiological signals in response to the delivery of notifications and other information presentation in an extended reality (XR) experience to determine whether the stimulus was perceived by the user. Some embodiments combine multiple streams of physiological data (e.g., skin conductance, heart rate, gaze trajectories, EEG, etc.) based on the users current activity and instantaneous motion measurements, such that measurements acquired at body sites that are more susceptible to motion artifacts carry less weight in the perception classification algorithm.

Example embodiments provide an XR system (or other system capable of presenting notifications) with automated perception confirmation of visual, auditory, haptic, gustatory and/or olfactory stimuli through detection of changes in users' physiological signals caused by the perception of the stimulus. These changes occur in response to the perception of the in-experience stimuli, which may be caused by the stimuli's sensory characteristics, psychophysiological impact and/or relevance to the user. In addition, example methods employ a context-dependent combination of physiological signals to improve signal quality and redundancy. Examples of such physiological signals include, but are not limited to, combinations of skin conductance, skin temperature, heart rate, respiration rate, pupil dilation, eye blink and gaze trajectories extracted using wearable and/or remote sensors.

In one example embodiment, an XR system or other system determines that there is a notification or other sensory information to be presented to the user. This information may be presented using a single sensory modality or a combination of different sensory modalities depending on the hardware available to the user. The system initiates the collection of multi-channel physiological signals using wearable and/or remote physiological sensing solutions prior to the presentation of the sensory information to gather contextualized baseline measurements. The system delivers the sensory information to the user using available peripherals, e.g., headset, hand controllers, and the like. The system collects the physiological signals until a prescribed time has passed post-stimulation. The system computes or otherwise determines appropriate features for each physiological sensing channel for the baseline measurements and from post-stimulation measurements. The system uses the users current application in combination with a context-based activity recognition system to estimate the likelihood of signal corruption for one or more of the physiological sensing channels. The likelihood of corruption may be represented in some embodiments by corruption likelihood coefficients. The system compares pre- and post-stimulation features per-channel to determine whether significant changes were caused by perceiving the stimulus. The corruption likelihood coefficients may be used to weight the contribution of each physiological sensing channel in the overall classifier. In some embodiments, this is performed using a meta-learning algorithm. If no difference or a sufficiently small difference is apparent between the pre- and post-stimulation features, this may be interpreted as an indication that the user has not perceived the stimulation. If, however, a difference is detected above a threshold (e.g. a statistical threshold) between the pre and post-stimulation features, this may be interpreted as an indication that the stimulus has been perceived. In some embodiments, further perceptual and experiential information such as changes in psychophysiological states may be extracted from the physiological signals by investigating effects within a channel and/or cross-channel effects. The system may then return a signal that indicates whether the information was perceived, along with, when applicable, the changes in psychophysiological state induced by the information being presented. The system may repeat the information presentation or other stimulation (e.g. in response to an indication that the information was not perceived), silence or otherwise dismiss the information (e.g. in response to an indication that the information was perceived), or take any other action as appropriate to its interaction objectives.

In some embodiments, there is no need for users to train, or even learn how to use the interface, since the system responds to natural changes in users' physiological states.

By automatically acknowledging the perception of information (e.g., notifications, messages or other stimuli) being delivered to users, the system may allow the users to remain focused on their primary task and preserve their cognitive budget for activities that are aligned with their current objective. For example, an email notification delivered during the design of a new product in an XR environment can be automatically dismissed based on the perception feedback provided by the proposed system, allowing users to allocate their cognitive reserves to their primary task.

In some embodiments, by offering a more natural means of interacting with, and automatically acknowledging the perception of in-experience stimuli, users can maintain better immersion in the XR experience. The psychophysiological feedback offered in some embodiments through the combination of multiple channels of physiological sensors allows for adaptation of the content to provide richer experiences to XR users.

To allow the confirmation of XR stimulus perception, example embodiments use at least one physiological sensor positioned adequately to acquire signals from a user. The physiological sensor(s) may be wearable, or they may use remote physiological sensing techniques. The sensors may be in communication with a processor or other computer controlling the XR experience, as illustrated in FIG. 2.

Figure 2:
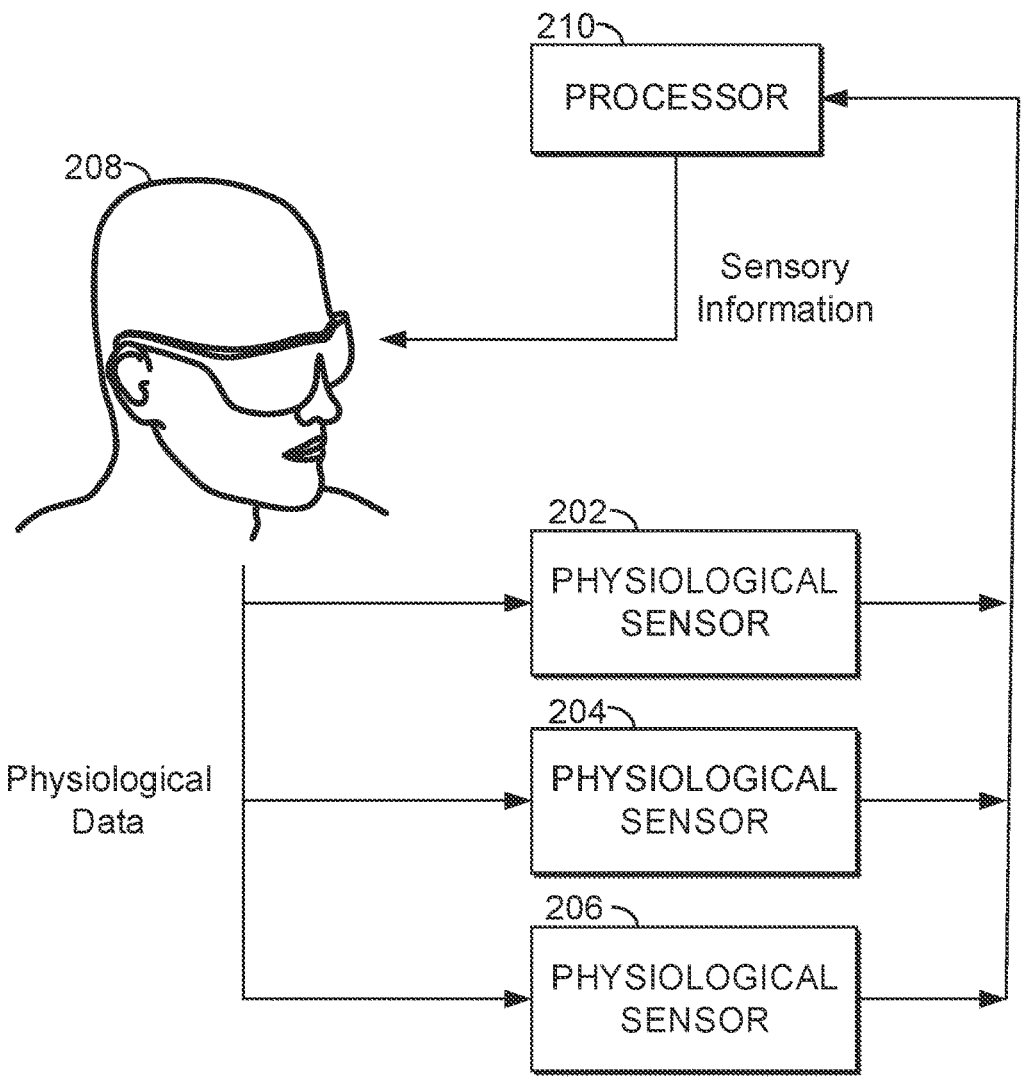
FIG. 2 is a schematic block diagram illustrating hardware architecture employed in some embodiments.

FIG. 2 is a schematic block diagram illustrating hardware architecture employed in some embodiments. In the example of FIG. 2, a plurality of physiological sensors 202, 204, 206 collect physiological data from a user 28 of an XR system. Data from the physiological sensors is provided to a processor 210 that is configured to perform any of the methods as described herein to determine whether a user has perceived an information item.

Figure 3:
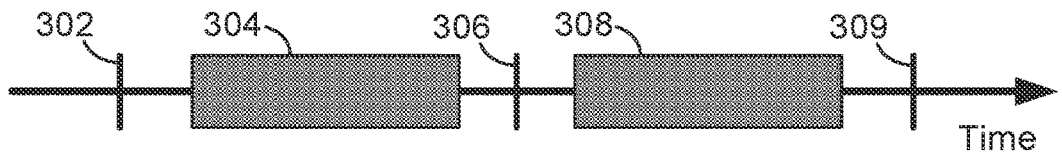
FIG. 3 is a visualization of a timeline of pre- and post-stimulation measurements used in some embodiments.

FIG. 3 is a visualization of a timeline of pre- and post-stimulation measurements used in some embodiments. At time 302, a determination is made to present an information item to a user. During period 304, baseline physiological measurements are collected. At time 306, the presentation of the information item to the user is initiated. During period 308 after initiation of the presentation of the information item, additional physiological measurements are collected. At time 309 a determination is made based on the physiological measurements of whether the user has perceived the information item, and that determination may be relayed to the system that presented the information item. For example, if a determination has been made that the information item has been perceived, then the item may be marked as read and/or may be dismissed.

Figure 4:
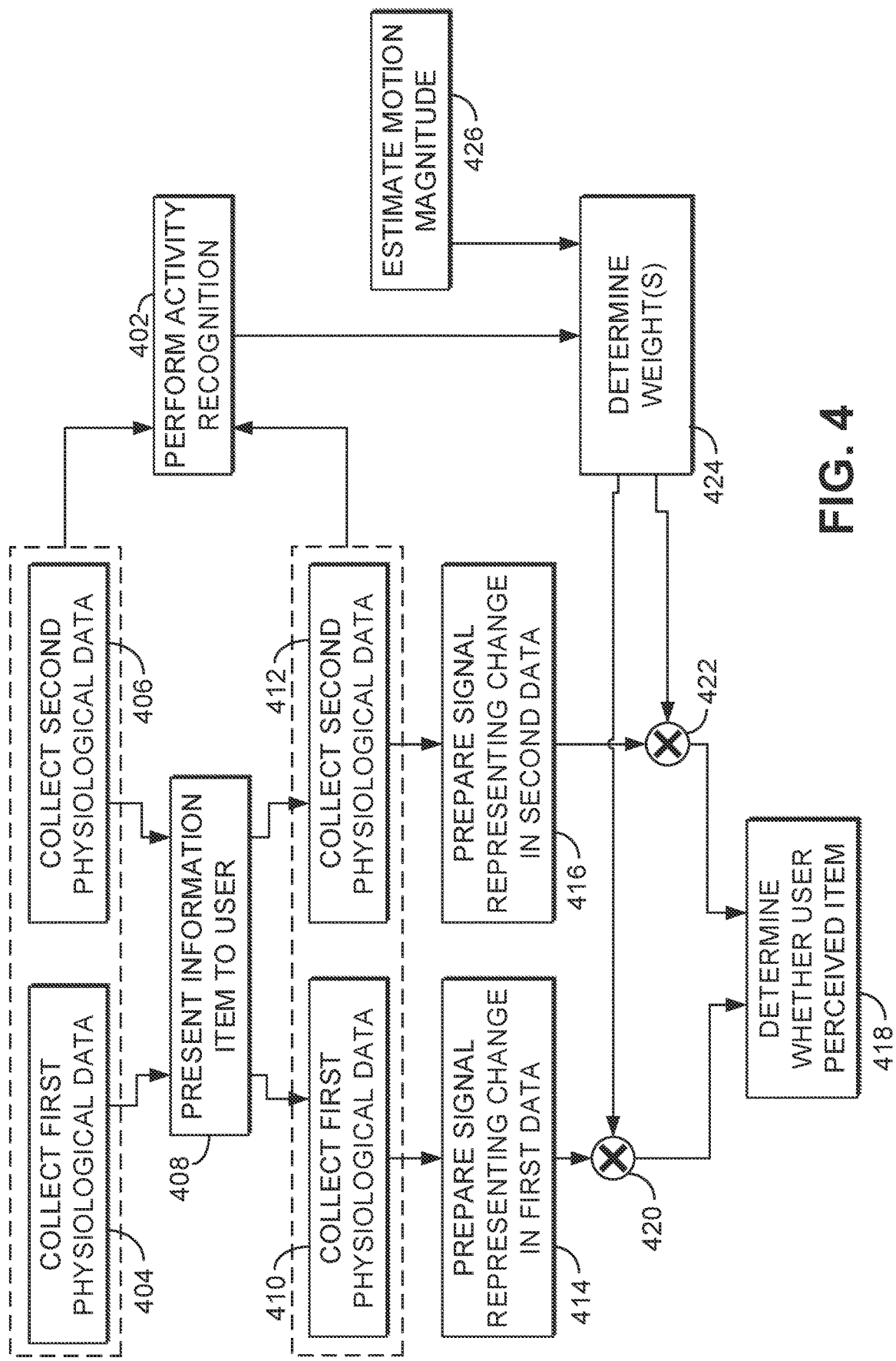
FIG. 4 is a flow diagram illustrating a method for confirmation of stimulus perception from physiological signals according to some embodiments.

In some embodiments, confirmation of stimulus perception from physiological signals may be achieved using the following procedure, as illustrated in FIG. 4.

The system (e.g. an XR controller) initiates physiological signal data collection before the presentation of the notification, message, haptic effect, or other sensory stimulus. In some embodiments, initiation of data collection may begin 1 to 10 seconds before the presentation, although other time periods may be used.

The exact amount of data collection time before and after stimulation may be dependent on the physiological signals used in a specific embodiment of the invention. For example, pupil dilation, EEG, heart rate and respiration signals operate on a much shorter time scale than skin conductance and skin temperature. Physiological signals that operate on a shorter time scale may be monitored for a shorter data collection time (e.g. 0.5-2 seconds), and physiological signals that operate on a longer time scale may be monitored for a longer data collection time (e.g. 1-8 seconds) to be able to make practical perception inference. In some embodiments, particularly if power consumption is not a concern, physiological signals may be continuously monitored and logged.

In some embodiments, contextual information is collected to predict the user's current activity and the users level of physical engagement in a current task. In some embodiments, the contextual information is collected simultaneously with the collection of pre-stimulation physiological signals. The collection of contextual information may be used to identify a discrete activity (e.g., standing up, walking, sitting, running, jumping) and combinations of discrete activities associated with the users task (e.g., in-place running and jumping, sitting and standing up, etc.). An initial set of signal corruption coefficients may be determined based on the identified discrete activity or activities (see Table 1 for examples). This information may be obtained directly from an analysis of the XR experience, or by using one or more known activity recognition frameworks.

TABLE 1

Example of activity-based initial corruption coefficient broken down by body location and physiological sensing modalities.

| Activity | Initial Corruption Coefficient |
|---|---|
| Sitting | Head |
|  |   Eye tracking, $Corr_{ET, I} = 0$ |
|  |   Pupillometry, $Corr_{pup, I} = 0$ |
|  |   EEG, $Corr_{EEG, I} = 0$ |
|  |   EOG, $Corr_{EOG, I} = 0$ |
|  |   fNIR, $Corr_{fNIR, I} = 0$ |
|  |   Skin temperature, $Corr_{skt, I} = 0$ |
|  | Upper body |
|  |   Abdominal respiration, $Corr_{AR, I} = 0$ |
|  |   Thoracic respiration, $Corr_{TR, I} = 0$ |
|  |   ECG, $Corr_{ECG, I} = 0$ |
|  | Hands/wrists |
|  |   Skin conductance, $Corr_{SCR, I} = 0$ |
|  |   Skin temperature, $Corr_{skt, I} = 0$ |
| Standing | Head |
|  |   Eye tracking, $Corr_{ET, I} = 0$ |
|  |   Pupillometry, $Corr_{pup, I} = 0$ |
|  |   EEG, $Corr_{EEG, I} = 0.20$ |
|  |   EOG, $Corr_{EOG, I} = 0.20$ |
|  |   fNIR, $Corr_{fNIR, I} = 0.25$ |
|  |   Skin temperature, $Corr_{skt, I} = 0$ |
|  | Upper body |
|  |   Abdominal respiration, $Corr_{AR, I} = 0$ |
|  |   Thoracic respiration, $Corr_{TR, I} = 0$ |
|  |   ECG, $Corr_{ECG, I} = 0$ |
|  | Hands/wrists |
|  |   Skin conductance, $Corr_{SCR, I} = 0.15$ |
|  |   Skin temperature, $Corr_{skt, I} = 0.15$ |
| Walking | Head |
|  |   Eye tracking, $Corr_{ET, I} = 0.15$ |
|  |   Pupillometry, $Corr_{pup, I} = 0.15$ |
|  |   EEG, $Corr_{EEG, I} = 0.35$ |
|  |   EOG, $Corr_{EOG, I} = 0.35$ |
|  |   fNIR, $Corr_{fNIR, I} = 0.40$ |
|  |   Skin temperature, $Corr_{skt, I} = 0.10$ |
|  | Upper body |
|  |   Abdominal respiration, $Corr_{AR, I} = 0.1$ |
|  |   Thoracic respiration, $Corr_{TR, I} = 0.1$ |
|  |   ECG, $Corr_{ECG, I} = 0.1$ |
|  | Hands/wrists |
|  |   Skin conductance, $Corr_{SCR, I} = 0.40$ |
|  |   Skin temperature, $Corr_{skt, I} = 0.35$ |

Some embodiments further operate to determine the user's level of physical engagement with the task at hand. In some embodiments, this is achieved by aggregating passive sensor data (e.g., accelerometer, gyroscope, magnetometer, motion tracking data, etc.) at one or more body locations to determine, given the discrete activity, which body parts are the most physically active during the user's activity and how active they are in relation to one another. For example, when sitting, the user's head usually experiences less motion than hands and upper body. However, in some cases, the user may be moving their head a lot because of an XR experience that calls for them to look around themselves. The resulting order may then be, from the less active to most active upper body, head, hands. A engagement-based corruption coefficient ranging between, for example, 0.75 and 1.25 may then be attributed based on the ranked list of active body parts, as shown in the example of Table 2.

TABLE 2

Example of ranked body location used to obtain the engagement-based corruption coefficient.

| Rank | Body site | Engagement-based Corruption Coefficient |
| --- | --- | --- |
| 1 (least motion) | Upper body (trunk) | 0.75 |
| 2 | Head | 1 |
| 3 (most motion) | Hands | 1.25 |

These results may be combined using, for example, the equation below to compute a corruption likelihood coefficient for each available physiological channel. The discrete activity may be used to obtain initial corruption likelihood coefficients for each physiological channel based on the user's activity. The physical engagement parameters may be used to customize the activity-based corruption coefficients such that they are better representative of the user's context. A weight array (w) used in the meta learning algorithm may be computed from the activity-based corruption coefficient array ($Corr_{Act}$) and engagement-based corruption coefficient array ($Corr_{Eng}$) using the following formula:

$$w = 1 - Corr_{Act} \cdot Corr_{Eng}'$$

The system (e.g. the XR controller) causes the sensory information to be presented to the user using the headset, haptic controller or any other relevant interface.

The system may stop collecting physiological data after stimulus presentation. For example, the system may stop collecting physiological data 5-15 seconds, or some other period, after stimulus presentation.

As illustrated in FIG. 4, an example method includes performing activity recognition 402 to determine an activity of a user. Data is collected (404) of a first physiological parameter before presentation of an information item, and data is collected (406) of a second physiological parameter before presentation of the information item. In some embodiments, the collection of physiological data before the presentation of the information item may be performed for between 1 and 10 seconds.

At 408, the presentation of an information item, such as a notification, is initiated. In some embodiments, the presentation of the notification may be delayed to allow collection of the physiological data. For example, in response to a determination to present physiological data, the data collection 404 and 406 may be initiated, and the notification may be presented to the user only after sufficient data has been collected to establish a baseline, e.g. between 1 and 10 seconds, or between 0.5 seconds to 8 seconds. The length of the delay and of the attendant data collection may depend on the physiological parameter(s) being collected. The use of a delay may help to limit the consumption of energy and computing resources that may otherwise be used in embodiments where physiological data is collected continuously.

After presentation of the information item has been initiated, additional data is collected (410) of the first physiological parameter, and additional data is collected (412) of the second physiological parameter. In some embodiments, the data collection after the presentation of the information item is initiated continues for between 5 and 15 seconds. In some embodiments, data collection of the physiological parameters may be continuous, with some data being collected before and some collected after the presentation of the information item is initiated. In some embodiments, the information item continues to be displayed after the presentation of the information item is initiated, and display of the information item may continue, for example, for a predetermined amount of time or until it is determined that the user has perceived the information item.

Based on the data collected regarding the first physiological parameter, a first signal is prepared or otherwise obtained (414) that represents a change in the first physiological parameter of the user between a time before and a time after presentation of an information item to the user. A second signal is prepared or otherwise obtained (416) that represents a change in the second physiological parameter of the user between a time before and a time after presentation of the information item to the user. In embodiments in which data is collected for additional physiological parameters, additional signals may be prepared or otherwise obtained that represent changes in those respective parameters between a time before and a time after presentation of the information item to the user.

The signals that represent changes in physiological parameters may be obtained using one or more of a variety of techniques. In some embodiments, the signal may represent a difference (including, e.g., an absolute value of a difference or a square difference) between a pre-stimulus average value of the parameter and a post-stimulus average value of the parameter, or between a pre-stimulus maximum or minimum, value of the parameter and a post-stimulus maximum or minimum value, or the like. In some embodiments, the signal may represent a difference between a pre-stimulus frequency of the parameter and a post-stimulus frequency of the parameter. In some embodiments, the signal may represent a difference between a pre-stimulus variability or range of the parameter and a post-stimulus variability or range of the parameter.

Using the first and second signals, a determination is made (418) of whether the user perceived the information item. In some embodiments, a contribution of the first signal to the determination is weighted (420), and/or a contribution of the second signal to the determination is weighted (422). In some embodiments, the strength (or other quantity) of the weights used for the first and/or second signal are determined (424) based on the users activity as determined by the activity recognition 402. In some embodiments, the weights are corruption coefficients or are determined based on corruption coefficients. In some embodiments, a measurement or other estimate is made of the magnitude of the user's motion (426), and the determination of the one or more of the weights is further based on an estimate of the magnitude of the motion.

The collected physiological signals may be pre-processed (e.g., filtered, cleaned, etc.) using existing automated signal cleaning procedures as deemed relevant depending on the physiological signal. For example, a band-pass filter may be applied to skin conductance measurements to a range of approximately 0.5-5 Hz to remove low frequency trends, noise introduced by small changes in pressure, and power frequencies (50-60 Hz). Signal correction methods may also be employed to automatically "correct" signal segments that are sensitive to motion artifacts or other large sources of noise.

Features may be extracted from one or more of the physiological sensing channels within the pre- and post-stimulation measurements. Such features may be dependent on specific physiological signals. Table 3 presents examples of such relevant features for examples of physiological signals. The physiological signals may be, but are not limited to, any combination of one or more of the following: skin conductance, photoplethysmography (PPG), electrocardiography (ECG), electroencephalography (EEG), electromyography (EMG), electrooculography (EOG), skin temperature, heat flux, abdominal and/or thoracic respiration, pupillometry and gaze tracking. These measurements may be achieved using, for example, traditional wearable sensors, head mounted display (HMD) integrated sensing apparatuses, or remote physiological sensing methods.

TABLE 3

Examples of possible features for a few examples of physiological signals.

| Physiological signal | Feature |
| --- | --- |
| Skin conductance | Skin conductance level, number of skin conductance responses (SCR), amplitude of SCR, latency of SCR, decay time of SCR, integral of SCR, descriptive statistics of the raw signal and features (e.g., mean, standard deviation, min, max, max-min, interquartile range, etc.) |
| Photoplethysmography (PPG) | Heart rate, pulse rate variability, waveform of the individual pulse, descriptive statistics of the raw signal and features (e.g., mean, standard deviation, min, max, max-min, interquartile range, etc.) |
| ECG | Heart rate, heart rate variability, waveform of individual pulse, descriptive statistics of the raw signal and features (e.g., mean, standard deviation, min, max, max-min, interquartile range, etc.) |
| Respiration | Respiration rate, respiration depth, difference between thoracic and abdominal respiration, respiration signal waveform, descriptive statistics of the raw signal and features (e.g., mean, standard deviation, min, max, max-min, interquartile range, etc.) |
| Pupil diameter | Oscillation of pupil diameter, descriptive statistics of the raw signal and features (e.g., mean, standard deviation, min, max, max-min, interquartile range, etc.) |
| Skin temperature | Skin temperature, number of skin temperature responses (STR), amplitude of STR, latency of STR, decay time of STR, integral of STR, descriptive statistics of the raw signal and features (e.g., mean, standard deviation, min, max, max-min, interquartile range, etc.) |

Figure 5:
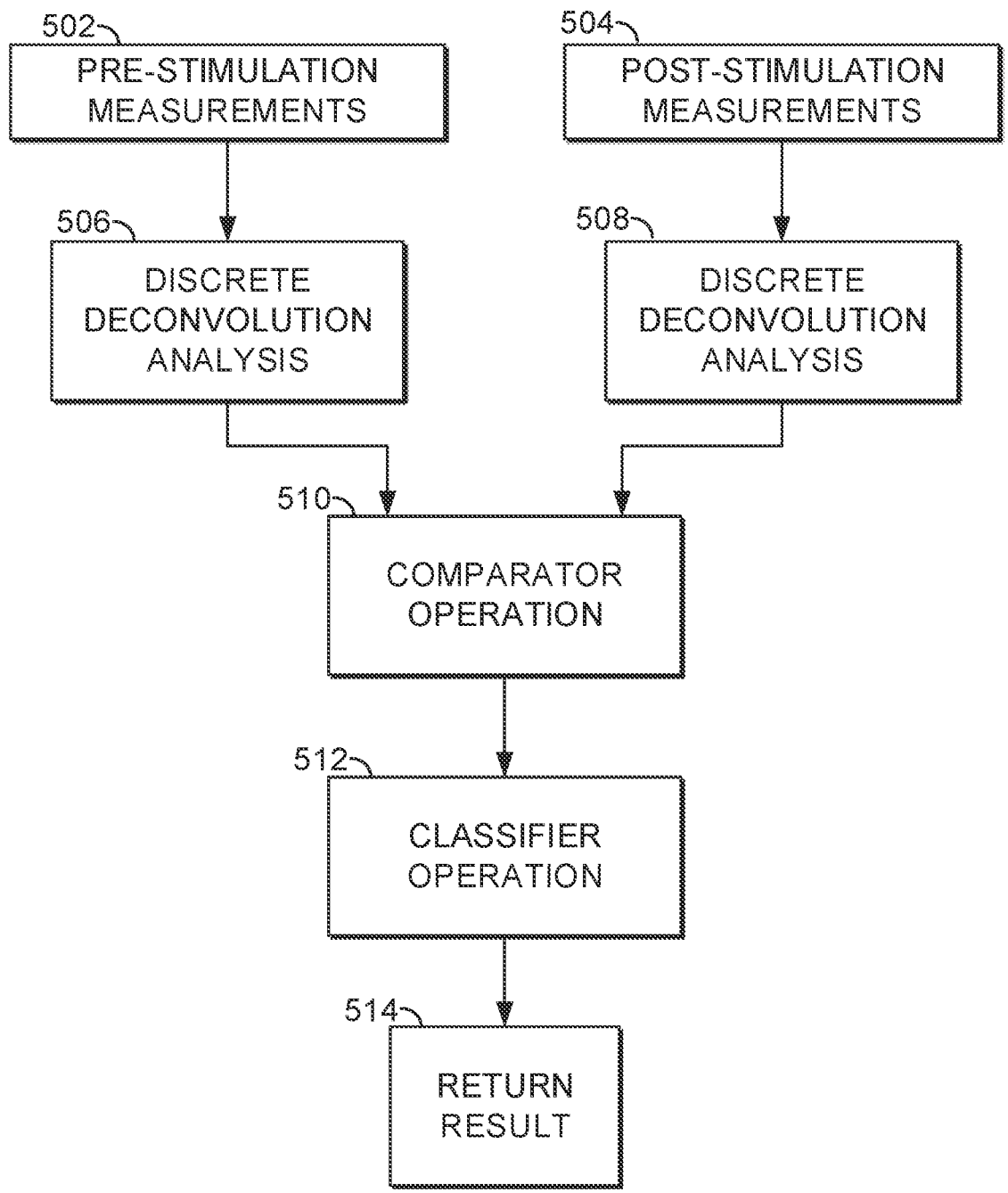
FIG. 5 is a flow diagram illustrating a method in which pre-stimulation and post-stimulation measurements are compared.

A binary classification algorithm or other technique may be employed to compare extracted features to determine, for each channel, whether the channel indicates that the stimulus was perceived by the user. FIG. 5 is an example illustrating a method in which pre-stimulation and post-stimulation measurements are compared, e.g. for skin conductance signals. The classification results for the available physiological channels may be combined using meta learning algorithms (e.g., ensemble methods or weighted majority algorithms) which may use the weights obtained above to increase the classification accuracy and reduce the impact of an individual channel on the classification outcome.

In an example method illustrated in FIG. 5, pre-stimulation physiological measurements (502) and post-stimulation physiological measurements (504) are collected for at least one physiological parameter. In this example, each of the physiological measurements is processed using discrete deconvolution analysis, although other preprocessing techniques may be used in other embodiments. At 510, a comparator compares the preprocessed signals to generate a signal representing a change in the physiological parameter of the user between a time before and a time after presentation of an information item to the user. At 512, a classifier operates to determine whether the user has perceived the stimulation, and at 514, the results of the classification are returned. The results may be used, for example, to determine whether to dismiss a notification and/or mark it as read in a case where the stimulus is a notification.

In some embodiments, in response to a determination that the information item was perceived, information from the different physiological signal channels may be combined to estimate the changes in psychophysiological states that they caused to the user. Interpretation of physiological signals may be performed using techniques such as those described in Jerritta, S., Murugappan, M., Nagarajan, R., & Wan, K., "Physiological signals based human emotion recognition: a review," in 2011 IEEE 7th International Colloquium on Signal Processing and its Applications (2011, March), pp. 410-415. A decision tree using increase or decrease of features between pre and post-stimulation may be used to provide an estimate of the users emotional state. More advanced machine learning methods may alternatively be applied to increase the emotion recognition accuracy.

The perception feedback may be relayed to the controller (e.g. XR controller) for further action.

In some embodiments, the processor receiving the physiological signals may be different from the one controlling the XR experience. In such case, a low latency communication channel may be established between the processors to provide timely initiation of physiological measurement and communication of the classification results.

In some embodiments, particularly where energy consumption is not an issue, the system may continuously measure physiological signals. In such embodiments, it may not be necessary for the system to wait for pre-stimulation measurements before presenting a stimulus, potentially making the overall process faster.

In some embodiments, particularly when the physiological signals have a high quality, richer information may be extracted from the physiological signals than a binary perception classification. In some embodiments, a classification is performed not only of whether a stimulus was perceived, but also how it was perceived, such as whether the stimulus negatively influenced the user's mood, cognitive load or other psychological construct.

Some embodiments may be implemented in an emergency alarm system. Residents in elderly and long-term health-care facilities often suffer from one or more sensory impairments. These sensory deficits may negatively impact their perception of emergency alarms (e.g., fire, carbon monoxide, evacuation order), to a point where they become partially or completely imperceptible. This introduces significant risks for the residents, but also for emergency responders that have to assist them. To address this issue, some facilities are equipped with visual indicators that activate simultaneously with the auditory alarms to catch the attention of residents with hearing impairments. However, not all facilities are equipped with such systems, nor does this resolve the perceptual challenges faced by individuals who also have visual impairments. In some embodiments, systems and methods are provided to confirm residents' perception of emergency alerts.

In an example of such an embodiment, residents may wear at least one physiological sensor in communication with a processor capable of implementing methods as described herein. When an alert is presented, this information may be communicated (e.g. simultaneously) to the patient's computing unit to activate the analysis of physiological signals. Alternatively, residents' physiological signals may be streamed by the processor to an intelligent alarm system to synchronize alarm presentation and residents' physiological responses.

In some embodiments, the residents' computing unit may be equipped with a microphone to capture and detect alarms. Once an alarm is detected, the perception prediction system may be activated to confirm whether the associated resident has perceived the alarm. The knowledge of which residents are aware of the alarm, combined with information on their mobility limitations and location may allow the care team and/or emergency responders to more efficiently organize an evacuation or otherwise direct emergency resources.

Some embodiments may be employed in the context of other types of alarms and alerts. For example, an embodiment used by a pedestrian or driver may operate to determine whether a user has perceived a car horn, an emergency vehicle siren, or a traffic or train signal, among other possibilities. The embodiment may operate to provide an additional alert to a user who has not perceived the outside stimulus. Some embodiments operate through communication, with, for example, an autonomous or semi-autonomous vehicle. In some embodiments, the vehicle may receive information from a system associated with a pedestrian or a driver of a different vehicle indicating whether that person perceived a particular stimulus, and the autonomous or semi-autonomous vehicle may use that information in its own operation. For example, the vehicle may give a wider berth or otherwise operate more cautiously around a pedestrian or a driver who has not been confirmed to have perceived an alert. In some embodiments, a system implemented in an autonomous or semi-autonomous vehicle may operate according to techniques described herein to determine whether its own driver and/or operator has perceived particular stimuli. Such a system may communicate that information to other vehicles and/or may use that information the operation of its own associated vehicle. For example, in response to a determination that the driver/operator has failed to perceive a stimulus, the vehicle may provide a higher level of automation and/or it may provide a supplemental alert (e.g. an audio signal or a light within the vehicle) that is more likely to be perceived by the user.

Some embodiments may be employed in an advertisement system. The pricing and effectiveness of advertisement campaigns are often based on anticipated "eyeball count" or similar measure. For example, an ad placed on a busy street will be more expensive, and is thought to be more effective, than one in a back alley, due to the number of people it is likely to reach. Some embodiments operate to confirm perception and/or interest towards an advertisement in, for example, an XR, web, TV, radio or physical environment.

In an example of such an embodiment, a viewer may wear at least one physiological sensor in communication with a processor capable of implementing methods as described herein. When an ad is presented, this information may be communicated to the viewers physiological sensing unit to activate the analysis of physiological signals. In some embodiments, viewers' physiological signals may be streamed to nearby intelligent advertisement hubs to synchronize ad presentation and their physiological responses.

In some embodiments, the viewer's physiological monitoring system may be equipped with a microphone, camera or other sensor system to capture and detect displayed ads. Once an advertisement is detected, the perception prediction system may be activated to confirm that it was perceived. In some embodiments, the system may estimate the viewer's interest towards the ad.

Depending on the physiological sensors available, different levels of perceptual information may be inferred. A single channel may suffice in some embodiments to determine whether an ad was perceived. However, as more channels are used, more granular perception inferences may be implemented to estimate, for example, whether the content was significant/relevant to the user and/or what emotions the content induced. Such information may be used, for example, in an advertisement pricing scheme based on the probability that an advertisement is perceived either because of its saliency, or its relevance to the viewer, as reported using techniques described herein. Such methods may also allow advertisers to present content tailored to the viewer's history of perceived advertisements, allowing for a continuity in the ad experience and better control over the campaign's effectiveness.

In some embodiments, this perception history may be combined with information on other viewer activities, such as their internet browsing and recent purchases. Beyond determining viewers' perception of advertisements and understanding customer behavior, such combination of data may be used in determining a physiological "purchase intent" index. Such an index may be iteratively updated over time to optimize its predictive performance for the general population as well as specific users/user groups.

Example Use Cases

A use case for some embodiments is in a collaborative XR meeting. In such an embodiment, a user may be engaged in a collaborative XR experience in which she and her colleagues are discussing a new smartphone prototype they are developing. They are standing in circle around a small table, interacting with the smartphone prototype using their hands. While the user is explaining a new feature that was added to the prototype, she receives an email from her boss, which triggers a notification (visual, auditory and haptic) in her XR display. At that moment, she is standing, moving her hands while her head and upper body remains relatively stable. The signal corruption coefficients resulting from the combination of the activity-based coefficient and the engagement-based coefficient results can be found in Table 4.

TABLE 4

Activity and engagement-based corruption coefficient computation.

| Activity | Initial Corruption Coefficient | Engagement-based Corruption Coefficient | Overall corruption coefficient | w |
|---|---|---|---|---|
| Standing | Head | | | |
| | Eye tracking, $Corr_{ET, I} = 0$ | 0.75 | 0 | 1 |
| | Pupillometry, $Corr_{pup, I} = 0$ | 0.75 | 0 | 1 |
| | EEG, $Corr_{EEG, I} = 0.20$ | Sensor unavailable | Sensor unavailable | N/A |
| | EOG, $Corr_{EOG, I} = 0.20$ | Sensor unavailable | Sensor unavailable | N/A |
| | fNIR, $Corr_{fNIR, I} = 0.25$ | Sensor unavailable | Sensor unavailable | N/A |
| | Skin temperature, $Corr_{skt, I} = 0$ | Sensor unavailable | Sensor unavailable | N/A |
| | Upper body | | | |
| | Abdominal respiration, $Corr_{AR, I} = 0$ | Sensor unavailable | Sensor unavailable | N/A |
| | Thoracic respiration, $Corr_{TR, I} = 0$ | Sensor unavailable | Sensor unavailable | N/A |
| | ECG, $Corr_{ECG, I} = 0$ | 1 | 0 | 1 |
| | Hands/wrists | | | |
| | Skin conductance, $Corr_{SCR, I} = 0.15$ | 1.25 | 0.185 | 0.815 |
| | Skin temperature, $Corr_{skt, I} = 0.15$ | Sensor unavailable | Sensor unavailable | N/A |

When perceiving the incoming email, the user's pupils dilate, her gaze is attracted towards the new information, her skin conductance peaks and her heart rate variability decreases. These changes in physiological signals are picked up by the system which uses them, with the weight array computed from the corruption coefficients, to determine that the user has perceived the incoming message. A schematic representation of the changes in each signal is provided in FIG. 6. In addition to the binary perception classification, the changes in her signals are classified and the system comes to the conclusion that this event was stress-inducing to her.

In an example where the XR system employs a perception feedback system, the message is automatically placed in the background once it is perceived. The fact that this was a stressful event for the user is integrated in the information presentation system. The system may then avoid presenting this type of information to avoid increasing the user's stress level, promoting a richer and more positive experience in the future. The user in this example may continue her explanation of the new feature without any of her colleagues noticing the reception and acknowledgment of the email.

Figure 6:
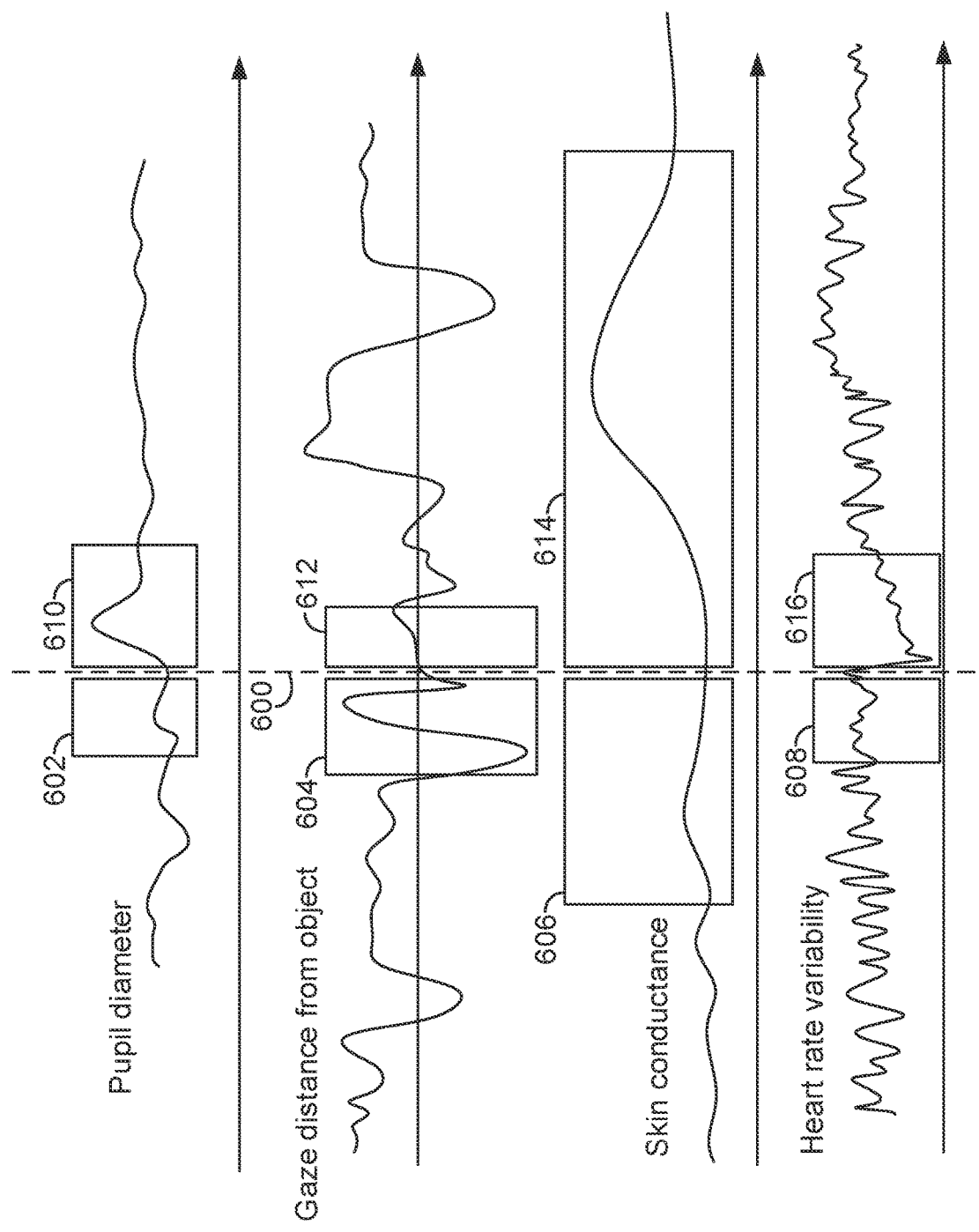
FIG. 6 is a schematic representation of physiological signals illustrating changes in each physiological signal following the perception of a piece of relevant information.

FIG. 6 is a schematic representation of physiological signals plotted over time illustrating changes in each physiological signal following the perception of a piece of relevant information in an XR environment. The time at which the information item is presented is illustrated by the dashed line 600. Physiological data collected before presentation of the information item is illustrated in regions 602, 604, 606, and 608. Physiological data collected after presentation of the information item is illustrated in regions 610, 612, 614, and 616. Comparison between physiological data collected before versus after the presentation of the information item is used in determining whether the user has perceived the information item.

Figure 7:
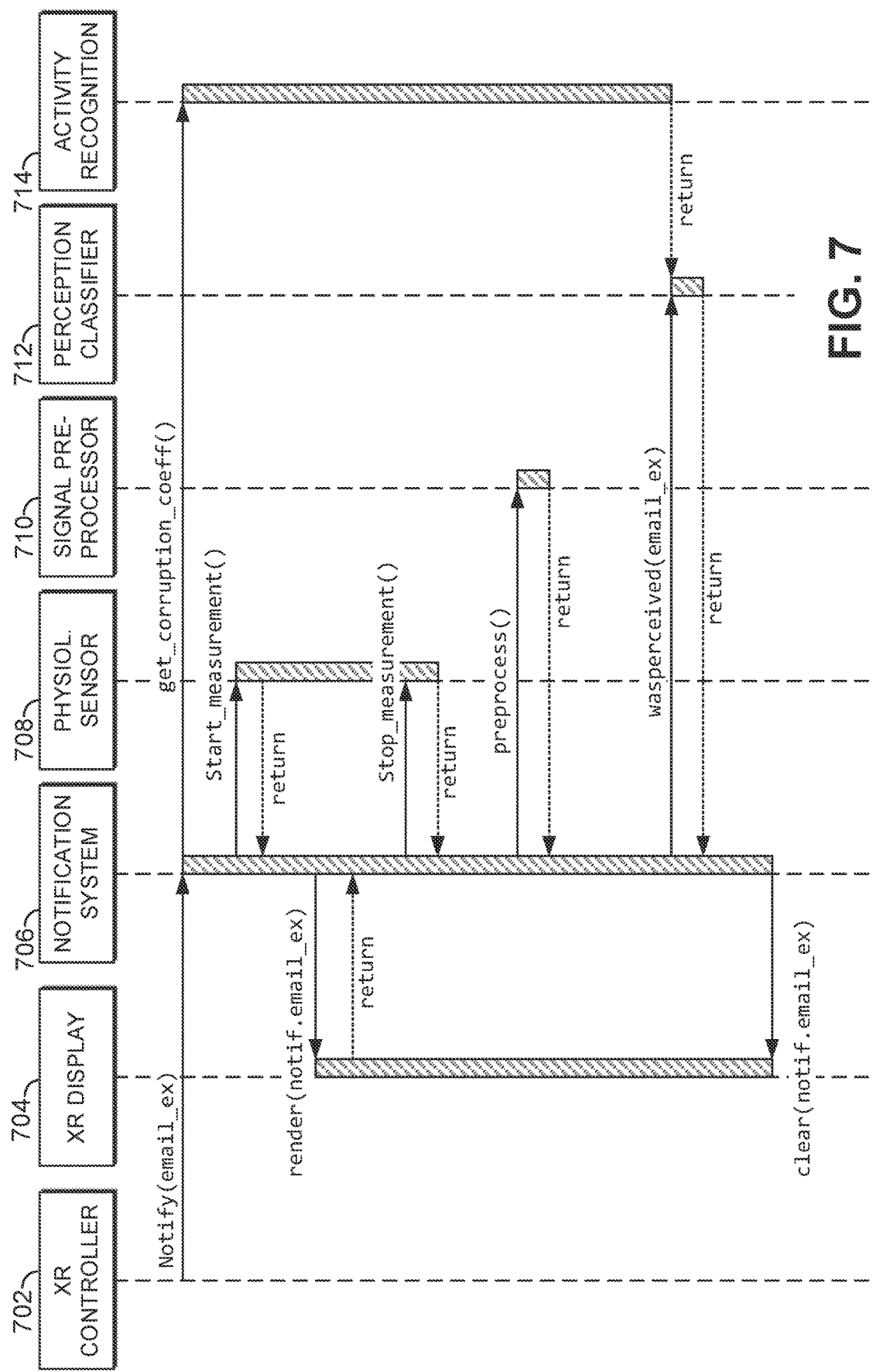
FIG. 7 is a sequence diagram illustrating a method performed in some embodiments.

FIG. 7 is a sequence diagram illustrating a method performed in some embodiments using an XR controller 702, an XR display 704, a notification system 706, at least one physiological sensor 708, a signal pre-processor 710, a perception classifier 712, and an activity recognition module 714. In an example method, the XR controller notifies the notification system of an event (e.g. an incoming email). The notification system requests corruption coefficient information from the activity recognition module. The notification system requests collection of physiological data from the physiological sensor. The notification system requests that the XR display render the notification. The notification system requests that the signal preprocessor process the collected physiological data. The notification system inquires of the perception classifier whether the notification was perceived. Based in part on the corruption coefficient(s) determined by the activity recognition module, the perception classifier determines whether the notification was perceived, and it informs the notification system of the result. If the notification is determined to have been perceived, the notification system requests that the XR display dismiss the notification.

Figure 8A:
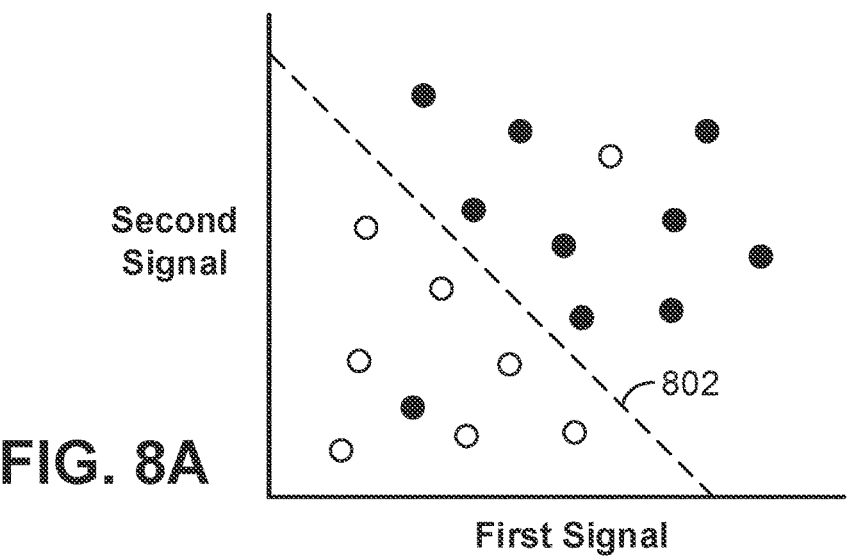
FIGS. 8A-8C are graphs schematically illustrating training and operation of a classifier with weighted inputs according to some embodiments.
Figure 8B:
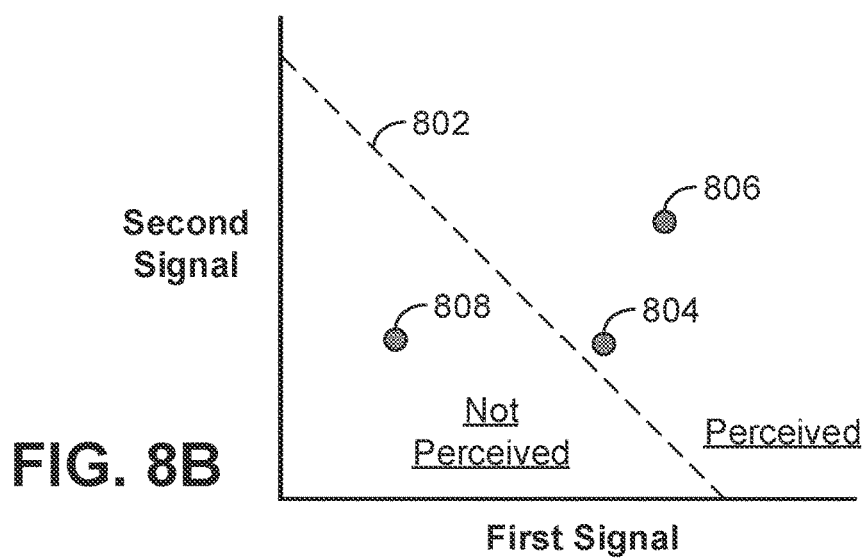
Figure 8C:
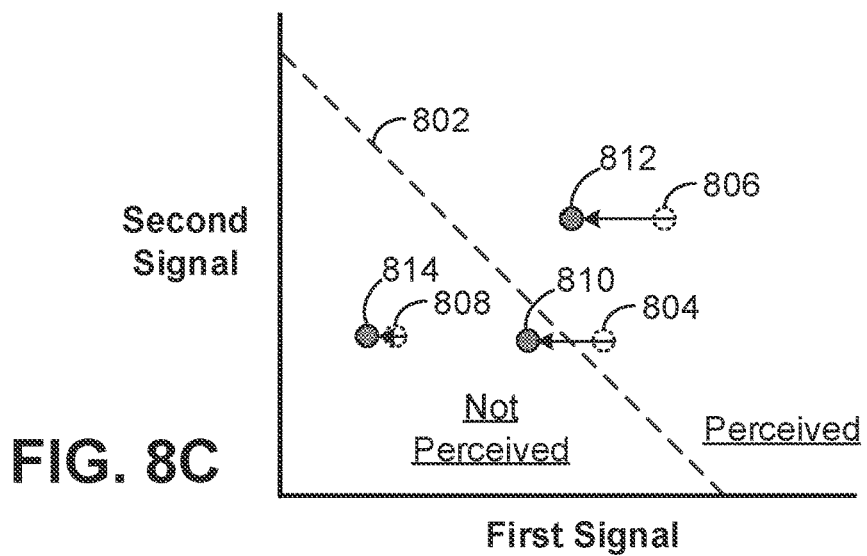

FIGS. 8A-8C are graphs schematically illustrating the training and use of a classifier according to some but not necessarily all embodiments. FIG. 8A is a graph schematically illustrating data collection for classifier training according to some embodiments. The horizontal axis represents a first signal representing a change in a first physiological parameter of the user between a time before and a time after presentation of an information item to the user. The vertical axis represents a second signal representing a change in a second physiological parameter of the user between a time before and a time after presentation of an information item to the user. Although FIGS. 8A-8C illustrate only two signals to allow for illustration on a two-dimensional page, it should be understood that the principles may be extended to the use of more than two physiological parameters.

Illustrated on the graph of FIG. 8A are several hypothetical data points of the type that may be collected from one or more individuals, with each data point being associated with a different stimulus. The position of the data point on the graph represents the values of the first and second signals. The color of the data points represents whether or not the individual perceived the stimulus, which may be based on reporting by those individuals during a training or experimentation phase. Filled circles represent stimuli that were perceived by the individual, and white circles represent stimuli that were not perceived. Based on the data, a boundary 802, which may be a line, curve, plane, or other surface as appropriate, may be fit to the data to separate regions representing perceived stimuli from regions representing un-perceived stimuli. As in the example of FIG. 8A, some data points may be outliers that do not strictly comply with the boundary.

Based on the boundary determined as described with respect to FIG. 8A, a system may operate to determine whether a user has perceived particular stimuli, including but not limited to XR notifications. In the example of FIG. 8B, various stimuli have been provided to a user at different times. For each of the stimuli, a first signal is obtained representing a change in the first physiological parameter of the user between a time before and a time after the respective stimulus, and a second signal is obtained representing a change in the second physiological parameter between a time before and a time after the stimulus. The resulting data points 804, 806, and 808 are shown on the graph of FIG. 8B. Based on the position of these data points relative to the boundary 802, a classifier may make a determination that the stimulus corresponding to data point 808 was not perceived but that the stimuli corresponding to data points 804 and 806 were perceived.

In some embodiments, as illustrated with respect to FIG. 8C, the classifier may apply weights to one or more of the signals. The weight(s) may be based on a determined activity of the user. Known techniques may be used to determine the activity of a user. For example, a combination of heartrate monitor, GPS, and accelerometer may be used to determine whether a user is walking, running, or otherwise exercising. Such activities may cause a user to sweat to varying degrees; accordingly, some physiological parameters such as skin conductance may become less representative of the user's psychological response during exercise-related activities, and the signal(s) related to such parameters may be weighted accordingly. In the example shown in FIG. 8C, the system obtains information indicating that the user is engaged in an activity that increases the likelihood of corruption of the first signal. For example, based on the activity, the system may determine that a corruption coefficient of 0.25 should be applied to the first signal. As a result, the system may apply a weight of 0.75 (=1−0.25) to the first signal. In some embodiments, weights are determined directly without the use of a corruption coefficient. When the weight is applied, data points 804, 806, 808 are repositioned to points 810, 812, 814. Using the weighted contribution of the first signal, the system may determine that the weighted signals represented by point 812 still correspond to a perceived notification, and that the weighted signals represented by point 814 still correspond to an un-perceived notification, but that the weighted signals represented by point 810 correspond to an un-perceived notification.

In some embodiments, when the contribution of one signal is reduced due to weighting, the contributions of other signals may be increased to normalize or otherwise balance the total contribution of signals. In some embodiments, the boundary used by the classifier may be shifted when weighted signals are used.

Additional Embodiments

A method according to some embodiments comprises: obtaining a first measurement of a first physiological parameter of a user from a time before presentation of an information item to the user; obtaining a second measurement of the first physiological parameter of the user from a time after a beginning of the presentation of the information item to the user; and determining, based at least on a comparison between the first measurement and the second measurement, whether the user has perceived the information item.

Some embodiments further include determining a first corruption coefficient corresponding to the first physiological parameter, wherein the determination of whether the user has perceived the information item is based at least in part on the first corruption coefficient. The first corruption coefficient may be based at least in part on an amount by which a current activity of the user is expected to interfere with the first physiological parameter.

Some embodiments further include obtaining a third measurement of a second physiological parameter of the user from a time before presentation of the information item to the user; and obtaining a fourth measurement of the second physiological parameter of the user from a time after the beginning of the presentation of the information item to the user; wherein the determination of whether the user has perceived the information item is further based on a comparison between the third measurement and the fourth measurement.

Some embodiments further include determining a first corruption coefficient corresponding to the first physiological parameter and a second corruption coefficient corresponding to the second physiological parameter, wherein the determination of whether the user has perceived the information item is based at least in part on the first corruption coefficient and the second corruption coefficient.

In some embodiments, the first corruption coefficient is based at least in part on an amount by which a current activity of the user is expected to interfere with the first physiological parameter and the second corruption coefficient is based at least in part on an amount by which a current activity of the user is expected to interfere with the second physiological parameter.

In some embodiments, the information item is a notification. In some embodiments, the information item is presented in an extended reality (XR) experience.

In some embodiments, at least one of the first and the second physiological parameter is a parameter selected from the group consisting of: skin conductance, photoplethysmography (PPG), electrocardiography (ECG), electroencephalography (EEG), electromyography (EMG), electrooculography (EOG), skin temperature, heat flux, abdominal and/or thoracic respiration, pupillometry and gaze tracking.

Some embodiments further include, in response to a determination that the user has perceived the information item, dismissing the information item.

In some embodiments, the time after a beginning of the presentation of the information item to the user is a time during the presentation of the information item to the user.

In some embodiments, the information item is an advertisement or an emergency alert.

An apparatus according to some embodiments comprises a processor configured to perform any of the methods described herein.

Various hardware elements of one or more of the described embodiments are referred to as "modules" that carry out (i.e., perform, execute, and the like) various functions that are described herein in connection with the respective modules. As used herein, a module includes hardware (e.g., one or more processors, one or more microprocessors, one or more microcontrollers, one or more microchips, one or more application-specific integrated circuits (ASICs), one or more field programmable gate arrays (FPGAs), one or more memory devices) deemed suitable by those of skill in the relevant art for a given implementation. Each described module may also include instructions executable for carrying out the one or more functions described as being carried out by the respective module, and it is noted that those instructions could take the form of or include hardware (i.e., hardwired) instructions, firmware instructions, software instructions, and/or the like, and may be stored in any suitable non-transitory computer-readable medium or media, such as commonly referred to as RAM, ROM, etc.

Although features and elements are described above in particular combinations, one of ordinary skill in the art will appreciate that each feature or element can be used alone or in any combination with the other features and elements. In addition, the methods described herein may be implemented in a computer program, software, or firmware incorporated in a computer-readable medium for execution by a computer or processor. Examples of computer-readable storage media include, but are not limited to, a read only memory (ROM), a random access memory (RAM), a register, cache memory, semiconductor memory devices, magnetic media such as internal hard disks and removable disks, magneto-optical media, and optical media such as CD-ROM disks, and digital versatile disks (DVDs). A processor in association with software may be used to implement a radio frequency transceiver for use in a WTRU, UE, terminal, base station, RNC, or any host computer.

What is claimed:

1. A method comprising:
   obtaining a first signal representing a change in a first physiological parameter of the user between a time before and a time after presentation of an information item to the user is initiated;
   obtaining a second signal representing a change in a second physiological parameter of the user between a time before and a time after presentation of the information item to the user is initiated;
   determining whether the user has perceived the information item, wherein the determination is based at least on the first signal, the second signal, and information indicating an amount of corruption of at least one of the first and second signals caused by a current activity of the user.

2. The method of claim 1, wherein obtaining the first signal comprises:
   obtaining a first measurement of the first physiological parameter of a user from a time before presentation of the information item to the user;
   obtaining a second measurement of the first physiological parameter of the user from a time after the presentation of an information item to the user is initiated; and
   generating the first signal based on a difference between the first measurement and the second measurement.

3. The method of claim 1, wherein the first signal is weighted based on a corruption coefficient associated with the current activity.

4. The method of claim 3, wherein the corruption coefficient is based at least in part on an amount by which the current activity of the user interferes with the first physiological parameter.

5. The method of claim 1, wherein determining whether the user has perceived the information item comprises applying a first weight to the first signal and a second weight to the second signal, the second weight being different from the first weight.

6. The method of claim 1, wherein the information item is a notification.

7. The method of claim 1, wherein the information item is presented in an extended reality (XR) experience.

8. The method of claim 1, wherein the first physiological parameter is a parameter selected from the group consisting of: skin conductance, photoplethysmography (PPG), electrocardiography (ECG), electroencephalography (EEG), electromyography (EMG), electrooculography (EOG), skin temperature, heat flux, abdominal respiration, thoracic respiration, pupillometry, and gaze tracking.

9. The method of claim 1, further comprising, in response to a determination that the user has perceived the information item, dismissing the information item.

10. A method comprising:
    in response to a determination to present an information item to a user, initiating a first measurement of a physiological parameter of the user for a first time period;
    delaying presentation of the information item to the user until after the first time period;
    conducting a second measurement of the physiological parameter for a second time period after initiation of the presentation of the information item to the user; and
    determining, based at least in part on a comparison between the first measurement and the second measurement, whether the user has perceived the information item.

11. The method of claim 10, further comprising, in response to a determination that the user has perceived the information item, dismissing the information item.

12. The method of claim 10, further comprising:
    obtaining information indicating a current activity of a user;
    wherein the determination of whether the user has perceived the information item is based at least in part on the current activity of the user.

13. An apparatus comprising a processor configured to perform at least:
    obtaining a first signal representing a change in a first physiological parameter of the user between a time before and a time after presentation of an information item to the user is initiated;
    obtaining a second signal representing a change in a second physiological parameter of the user between a time before and a time after presentation of the information item to the user is initiated;
    determining whether the user has perceived the information item, wherein the determination is based at least on the first signal, the second signal, and information indicating an amount of corruption of at least one of the first and second signals caused by a current activity of the user.

14. The apparatus of claim 13, wherein obtaining the first signal comprises:
    obtaining a first measurement of the first physiological parameter of a user from a time before presentation of the information item to the user;
    obtaining a second measurement of the first physiological parameter of the user from a time after the presentation of an information item to the user is initiated; and
    generating the first signal based on a difference between the first measurement and the second measurement.

15. The apparatus of claim 13, wherein determining whether the user has perceived the information item comprises applying a first weight to the first signal and a second weight to the second signal, the second weight being different from the first weight.

16. The apparatus of claim 13, wherein the first signal is weighted based on a corruption coefficient associated with the current activity.

17. The apparatus of claim 16, wherein the corruption coefficient is based at least in part on an amount by which the current activity of the user interferes with the first physiological parameter.

18. The apparatus of claim 13, wherein the information item is a notification.

19. The apparatus of claim 13, wherein the information item is presented in an extended reality (XR) experience.

20. The apparatus of claim 13, wherein the information item is dismissed in response to a determination that the user has perceived the information item.

* * * * *